United States Patent
Bouzigues et al.

(10) Patent No.: US 10,788,497 B2
(45) Date of Patent: Sep. 29, 2020

(54) METHOD FOR DETECTING OXIDISING SPECIES

(71) Applicants: ECOLE POLYTECHNIQUE, Palaiseau (FR); CENTRE NATIONAL DE LA RECHERCHE SCIENTIFIQUE, Paris (FR)

(72) Inventors: Cédric Bouzigues, Paris (FR); Mouna Abdesselem, Bourg la Reine (FR); Antigoni Alexandrou, Palaiseau (FR); Thierry Gacoin, Bures sur Yvette (FR); Jean-Pierre Boilot, Meudon (FR)

(73) Assignees: ECOLE POLYTECHNIQUE, Palaiseau (FR); CENTRE NATIONAL DE LA RECHERCHE SCIENTIFIQUE, Paris (FR)

( * ) Notice: Subject to any disclaimer, the term of this patent is extended or adjusted under 35 U.S.C. 154(b) by 6 days.

(21) Appl. No.: 15/747,888

(22) PCT Filed: Jul. 28, 2016

(86) PCT No.: PCT/EP2016/068096
§ 371 (c)(1),
(2) Date: Jan. 26, 2018

(87) PCT Pub. No.: WO2017/017233
PCT Pub. Date: Feb. 2, 2017

(65) Prior Publication Data
US 2018/0217149 A1    Aug. 2, 2018

(30) Foreign Application Priority Data

Jul. 29, 2015  (FR) ...................................... 15 57275

(51) Int. Cl.
*G01N 33/58* (2006.01)
*G01N 21/64* (2006.01)
*G01N 33/50* (2006.01)

(52) U.S. Cl.
CPC ....... *G01N 33/582* (2013.01); *G01N 21/6428* (2013.01); *G01N 21/6458* (2013.01); *G01N 21/6489* (2013.01); *G01N 33/5038* (2013.01); *G01N 33/5091* (2013.01); *G01N 2458/30* (2013.01); *G01N 2458/40* (2013.01); *G01N 2800/7009* (2013.01)

(58) Field of Classification Search
CPC .................................................. G01N 33/582
See application file for complete search history.

(56) References Cited

PUBLICATIONS

Chen et al., "Upconversion nanoprobes for efficiently in vitro imaging reactive oxygen species and in vivo diagnosing rheumatoid arthritis", Biomaterials, vol. 39, pp. 15-22; e-Publication: Nov. 2014. (Year: 2015).*
Chvanov et al., "Novel Lipophilic Probe for Detecting Near-Membrane Reactive Oxygen Species Responses and Its Application for Studies of Pancreatic Acinar Cells: Effects of Pyocyanin and L-Ornithine", Antioxidants & Redox Signaling, vol. 22, pp. 451-464; e-Publication: Feb. 2015. (Year: 2015).*
International Search Report for corresponding International Application No. PCT/EP2016/068096 dated Nov. 24, 2016.
Casanova et al., "Single eruopium-doped nanoparticles measure temporal pattern of reactive oxygen species production inside cells" Nature Nanotechnoogy; Sep. 2009, vol. 4, No. 9, pp. 581-585, XP055027045.
Abdesselem et al, "Multifunctional Rare-Earth Vanadate Nanoparticles: Luminescent Labels, Oxidant Sensors, and MRI Constrast Agents", ACS NANO, vol. 8, No. 11, Nov. 25, 2014, pp. 11126-11137, XP055275081.
English translation of the Written Opinion for corresponding International Application No. PPCT/EP2016/068096 dated Nov. 24, 2016.
English translation of the Abstract for Bouzigues et al., "Cartogrpahier la concentration intracellulaire d'espèces oxygénées réactives", M/S Medecine Sciences, vol. 30, No. 10, Oct. 1, 2014, pp. 848-850, XP055275410 previously submitted on Jan. 26, 2018).

* cited by examiner

*Primary Examiner* — Michelle F. Paguio Frising
(74) *Attorney, Agent, or Firm* — Pearne & Gordon LLP

(57) ABSTRACT

A method which can be used to analyse oxidising species in a sample, including: placing the sample in contact with a first photoluminescent agent, and a second optically active agent, at least the first photoluminescent agent including nanoparticles doped with rare earth elements and being oxidisable, the luminescence of the first photoluminescent agent varying, at least at one first wavelength, with the amount of oxidising species, and the signal emitted by the second optically active agent being constant or varying, at least at one second wavelength other than the first wavelength, with the amount of oxidising species in a direction opposite to the luminescence of the first photoluminescent agent; energising the first and second agents in the sample; measuring the light intensity of the sample at least at the first and second wavelengths; and assessing the presence and/or the amount of oxidising species by interpreting the measured light intensities.

26 Claims, 8 Drawing Sheets

METHOD FOR DETECTING OXIDISING SPECIES

FIELD

The invention relates to a method that can be used for analyzing oxidizing species and to a system for detecting oxidizing species, suitable for implementing this method.

BACKGROUND

A great many methods have already been proposed that aim to detect the presence of oxidizing species in a sample.

The oxidizing species more particularly targeted are notably cellular messengers involved in various signaling pathways. Their regulation is crucial in immune reactions and in pathologies such as certain cancers, cardiovascular diseases or neurodegenerative diseases. It is therefore advantageous to have effective methods at our disposal for determining the presence, quantifying said presence and the variation over time of the concentration of oxidizing species in a test sample, notably in a biological sample.

It should be noted, however, that the detection of oxidizing species has many other applications. Thus, as an example, application FR-A-2 980 847 presents a method for detecting explosives based on the detection of oxidizing species.

Some of the known methods propose the use of an organic fluorescent agent (or fluorophore) whose luminescence is intensified by the presence of oxidizing species in the sample. DiChloroFluorescein is an example of an organic fluorescent agent of this kind, whose fluorescence is intensified in the presence of an oxidant, and which can be used in a living environment.

However, it is known that an organic fluorescent agent of this kind undergoes strong photobleaching and is liable to oxidize spontaneously in the ambient environment, which makes it impossible in practice to perform long-term quantitative measurements. Furthermore, the increase in fluorescence follows an irreversible oxidation reaction, which does not allow time-resolved measurements to be performed.

The use of a fluorescent protein as the fluorescent agent, notably in a genetically modified organism, is also known. cpYFP, HyPer (1, 2 and 3) or roGFP are known examples of a fluorescent protein of this kind. However, these agents may be specific to certain oxidizing species only, may have a long response time or have a limited range of detection, with for example saturation at 500 nmol.L$^{-1}$ for the best-performing of the Hyper proteins, Hyper3, which is incompatible with certain applications, notably biological applications. However, Bilan et al., ACS Chem. Biol 2013 showed that these fluorescent proteins could be used for detecting oxidizing species in living cells, but without obtaining a measurement of the absolute concentration of oxidants.

Moreover, a method for quantitative detection of oxidizing species in which nanoparticles of $Y_{0.6}Eu_{0.4}VO_4$ doped with europium in oxidation state III are used as the photoluminescent agent is known from the article "Single europium-doped nanoparticles measure temporal pattern of reactive oxygen species production inside cells", by Didier Casanova et al., Nature Nanotechnology, Vol. 4, September 2009. The use of these particles therefore requires their reduction beforehand, to make them oxidizable. This reduction is performed there in situ under laser irradiation so as to have the europium element with oxidation number II and therefore in a form that is oxidizable by one or more oxidizing species. Now, this photoreduction for the purpose of generating the oxidizable europium species sometimes proves harmful to the cells that are also present. This photoreduction is, moreover, difficult to achieve on macroscopic samples or in vivo.

Furthermore, for determining the temporal variation of the concentration of oxidizing species in the sample tested, the method described in that article requires determination of the luminous intensity of the nanoparticles and the derivative of this signal with respect to time. Determination of this derivative requires several successive measurements of the luminous intensity, which limits the temporal resolution of such a method to about 30 s.

Finally, such a method is based on measurement of an absolute intensity of luminescence and therefore assumes observation of the nanoparticles in an individualized manner, which prevents any detection in a macroscopic volume.

The aim of the present invention is to propose a method for detecting oxidizing species that does not have the drawbacks of the methods known from the prior art. Notably, the invention aims to propose a method that is compatible with bulk measurement and/or has a better temporal resolution and, according to a preferred variant, does not require generation of an oxidizable species in situ.

SUMMARY

For this purpose, the invention mainly proposes a method that can be used for analyzing oxidizing species in a sample, in particular in a biological sample, comprising the steps consisting of:
  i) contacting the sample with a photoluminescent first agent, and an optically active second agent, the photoluminescent first agent at least comprising nanoparticles doped with rare earths and oxidizable, with
    the luminescence of the photoluminescent first agent varying, at at least one first wavelength, with the quantity of oxidizing species, and
    the signal emitted by the optically active second agent being constant or varying, at at least one second wavelength different from the first wavelength, with the quantity of oxidizing species and in a direction opposite to the luminescence of the photoluminescent first agent,
  ii) exciting the photoluminescent first agent and the optically active second agent in the sample;
  iii) measuring the luminous intensity of the sample at at least said first wavelength and at least said second wavelength, and
  iv) estimating the presence and/or the quantity of oxidizing species by interpreting said measured luminous intensities, and if applicable by reference to standard values.

In the sense of the invention, the expression "analysis of oxidizing species" covers the aspect of detection or qualitative characterization of the presence or absence of oxidizing species as well as the aspect of assay or quantitative characterization of the oxidizing species.

In the sense of the invention, optically active agent means an agent that emits photons following excitation by photons, optionally of different wavelengths.

Thus, the method proposed is based on the simultaneous measurement of the intensity of emission of a photoluminescent first agent and of an optically active second agent, the intensity of emission of at least one of the two agents varying as a function of the presence of oxidizing species. Double simultaneous measurement is possible by selecting agents having different emission wavelengths. The inventors have demonstrated furthermore that this double measurement makes it possible to perform measurements in bulk on a macroscopic or a microscopic sample, with better temporal resolution, as will be explained in more detail hereunder.

More precisely, the first wavelength corresponds to an emission wavelength representative of the oxidized form or of the reduced form of the photoluminescent first agent.

For its part, the second wavelength corresponds to an emission wavelength specific to the optically active second agent and, if applicable, representative of its reduced or oxidized form.

According to a preferred variant, the first luminescence wavelength is representative of an oxidized form of the photoluminescent first agent. Consequently, the presence of oxidizing species will be confirmed by the visualization of an enhanced luminous intensity at this wavelength.

According to a first variant, the luminescent first agent is used in combination with an optically active agent whose luminous intensity does not vary with the concentration of oxidizing species. In this alternative, the luminous intensity specific to the optically active agent may be used directly as a standard value for confirming whether or not there is an increase in the luminous intensity specific to the luminescent first agent, any increase revealing the presence of at least one oxidizing species.

This embodiment based on the combination of the luminescent first agent with an optically active second agent is particularly advantageous for analysis in a macroscopic volume and notably in a non-surface environment, for example a liquid volume or in a sample thickness.

According to a second variant, the luminescent first agent is used in combination with an optically active agent for which the luminous intensity of said accredited second wavelength also varies as a function of the concentration of oxidizing species but in a manner opposite to that displayed by the luminescent first agent. The nanoparticles of the two types are observed individually, for example after deposition on a surface or internalization in a cell. Thus, in the preferred variant of the method according to the invention in which the first luminescence wavelength is representative of an oxidized form of the photoluminescent first agent, the second wavelength specific to the optically active agent is representative of the reduced form of this agent. Thus, the presence of oxidizing species will be confirmed by visualization of a decrease in the luminous intensity of this second wavelength.

In this alternative, interpretation of the measurements of the two luminous intensities is advantageously performed with reference to preestablished standard values.

More precisely, the quantity of oxidizing species in the sample may be determined by reading, on a standard sheet, the value corresponding to the pair of luminous intensities measured in step iii). This standard sheet is a sheet established beforehand by means of measurements performed with samples with a known quantity of oxidizing species, preferably in conditions identical to those in which the sample is investigated, these identical conditions notably including at least one of: the solvent, the pH and the test temperature.

This embodiment based on the combination of the luminescent first agent with an optically active second agent with variable luminous intensity is particularly advantageous, in that it makes it possible to obtain, from a single measurement of the pair with luminous intensity representative of the first and second agents, and therefore rapidly, limited only by the acquisition rate of the recording device, and furthermore reliably, a quantitative value of the concentration of oxidizing species in the analysis sample.

According to one embodiment, the method according to the invention employs, as the photoluminescent first agent, nanoparticles of $A_x Eu_{1-x}(VO_4)_y(PO_4)_{(1-y)}$, in particular $A_x Eu_{1-x} VO_4$, where A is one from Y, Gd and La, $0 \leq x \leq 1$ and $0 \leq y \leq 1$ in which the element europium is at least partially in a reduced state and therefore has an oxidation number II.

Taking into account the presence of the element europium in the reduced oxidation state, the corresponding nanoparticles are advantageously directly oxidizable as opposed to nanoparticles of $A_x Eu_{1-x}(VO_4)_y(PO_4)_{(1-y)}$, called oxides, as they contain the element Eu solely in an oxidation state III.

Thus, according to another of its aspects, the invention also relates to a method that can be used for analyzing oxidizing species in a sample, in particular in a biological sample, comprising the steps consisting of:
  i) providing oxidizable photoluminescent nanoparticles of $A_x Eu_{1-x}(VO_4)_y(PO_4)_{(1-y)}$, where A is one from Y, Gd and La, $0 \leq x \leq 1$ and $0 \leq y \leq 1$ and containing the element europium with oxidation number II,
  ii) introducing said nanoparticles into the assay sample,
  iii) exciting said nanoparticles,
  iv) measuring the luminous intensity emitted by the sample at at least one wavelength representative of the oxidized form or of the reduced form of said nanoparticles, and
  iv) estimating the presence and/or the quantity of oxidizing species by interpreting said measurement, if applicable by reference to a standard or calibration.

A method according to the invention is particularly useful for the analysis, notably the detection and/or assay of oxidizing species in a sample.

Thus, a method according to the invention may be employed for studying the ecological impact of discharges of oxidants from industrial processes for cleaning and bleaching. It may also allow detection of oxidizing species in the vapor phase for detecting explosives.

However, the methods according to the invention are quite particularly of interest for the characterization of reactive oxygen species (ROS), of relevance in the field of life sciences.

Thus, according to another of its aspects, the present invention relates to the use of a method according to the invention for purposes of diagnosis, notably of physiological disorders, whether or not pathological, associated with expression of one or more reactive oxygen species that is not physiologically acceptable.

In fact, the reactive oxygen species are essential and are involved in a large number of biological functions, mainly signal transduction, neurotransmission, relaxation of smooth muscles, platelet aggregation, modulation of arterial pressure, control of the immune system, regulation of cellular growth, synthesis of numerous biological molecules, inflammation and the metabolism of xenobiotics.

As representative examples of the reactive oxygen species that may be analyzed in a biological sample, we may notably mention free radicals such as the superoxide ($O_2^{.-}$) hydroperoxide ($HO_2^{.-}$), hydroxyl (HO.), peroxide (ROO.), nitrogen monoxide (NO.), and nitrogen dioxide ($NO_2$) radicals, but also the non-radical species such as hydrogen peroxide ($H_2O_2$), singlet oxygen ($^1O_2$), hypochlorous acid (HOCl), the peroxynitrite anion ($ONOO^-$), peroxynitrous acid (ONOOH), the nitrosoperoxycarbonate anion ($ONOOCO_2^-$), the nitronium cation ($NO_2^+$) and nitrogen trioxide ($N_2O_3$), for example.

Consequently, when these oxidizing species are produced in excess or conversely when their physiological content proves insufficient, this leads to physiological disorders in the form of oxidation of biological molecules such as certain proteins, for example. Similarly, characterization of an amount inconsistent with the usual physiological levels may be an indicator of the manifestation of a metabolic dysfunction or of a pathological state such as inflammation, for example.

Thus, a method according to the invention may allow efficient assay of the amount of one or more oxidizing species in a biological sample and of confirming, on the basis of the measurement performed, whether the concentration of these species is or is not physiologically acceptable.

A biological sample may notably be for example a living organism, or biological tissues, notably isolated from any living organism (ex vivo or fixed tissues), cells, or else a solution notably containing biological molecules.

The fact that the method is effective at a volume scale makes it possible to use it at the level of a biological target in vivo or of an extract of tissues or of biological fluid.

Thus, the method according to the invention is advantageously carried out on a volumetric sample and is compatible with use in vivo, ex vivo and in vitro. As an example of use, it is possible to perform a measurement using a vessel containing the sample to be analyzed. The two agents are added thereto in solution, excited by specific sources, and the luminous intensity associated with each is collected on two photomultipliers. As for analysis of a tissue, this may be carried out by injection of the mixture of nanoparticles and detection with spectral separation on a macroscope.

According to a particular embodiment, the method according to the invention is employed for an ex vivo use for purposes of diagnosis, notably of physiological disorders, whether or not pathological, associated with expression of one or more reactive oxygen species that is not physiologically acceptable.

According to yet another of its aspects, the present invention relates to the use, in particular ex vivo, of a method according to the invention for purposes of screening the efficacy of an active substance with respect to a disorder, whether or not pathological, and associated with overexpression of one or more reactive oxygen species (ROS).

Thus, a method according to the invention may be used for analyzing the quantity of oxidizing species in a biological sample obtained from a patient treated with a therapeutic active substance and estimating the value of the measurement thus obtained by comparing against a reference value representative for example of a biological sample from the same patient but before treatment.

This type of screening may also be carried out experimentally for laboratory testing of a panel of potential active substances whose efficacy may be confirmed via assay of oxidizing species, evaluated in their presence and in their absence.

According to another aspect, the invention proposes a system for implementing a method according to the invention comprising:

a device for laser illumination at one or two wavelengths for exciting the photoluminescent first agent and the optically active second agent in the sample, a spectrum splitter for filtering the emissions from the photoluminescent first agent and the optically active second agent according to different wavelengths, thus forming two separate filtered images of the sample, and means for determining the luminous intensity of at least points of the two filtered images.

BRIEF DESCRIPTION OF THE DRAWINGS

The invention will be better understood on reading the following description, given only for purposes of illustration, and nonlimiting, referring to the appended drawings, where.

DETAILED DESCRIPTION

Figure 1:
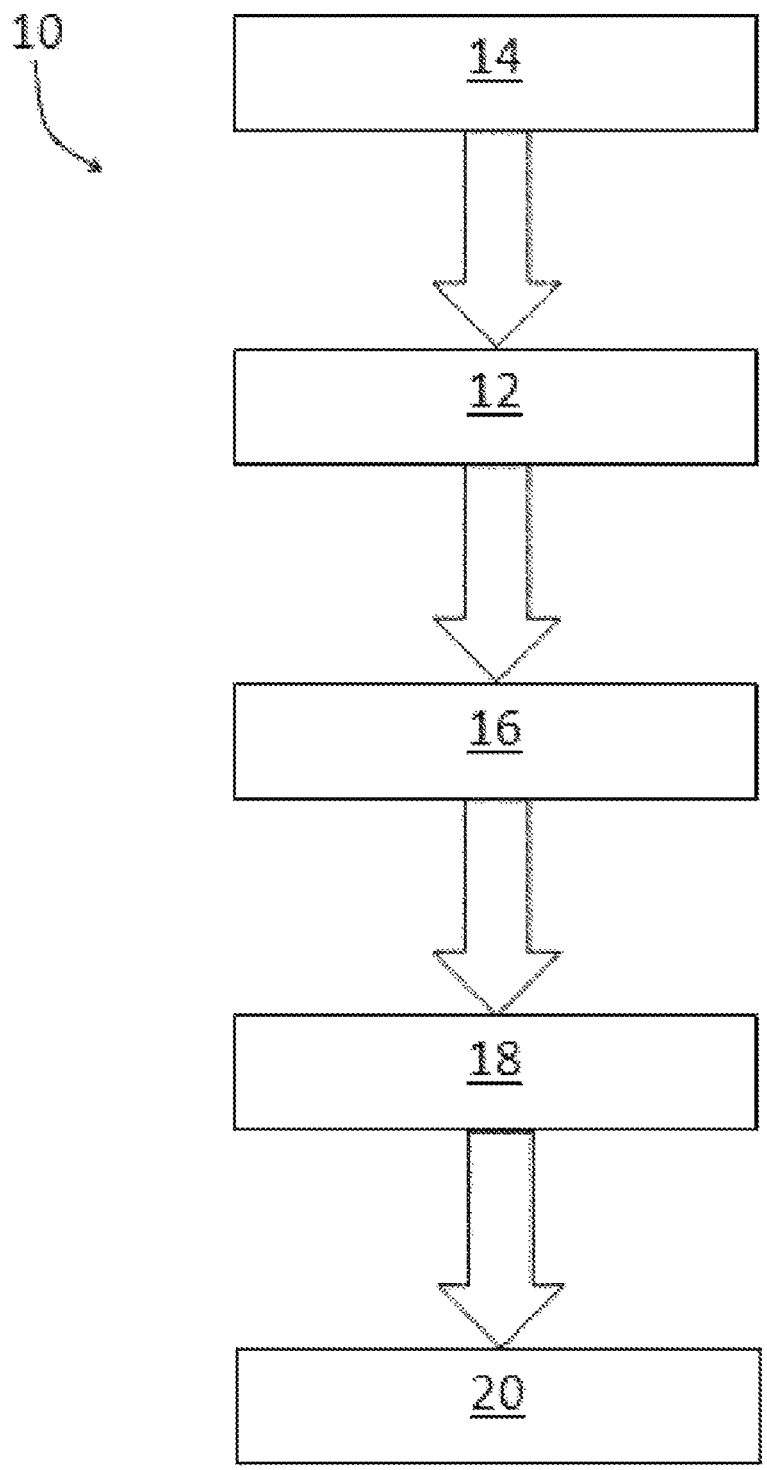
FIG. 1 shows a functional diagram of a method for detecting oxidizing species.

The method for detecting oxidizing species 10 comprises a first step 12 of contacting the sample with a photoluminescent first agent and an optically active second agent.

As stated above, optically active agent means an agent that emits photons following excitation by photons, optionally of different wavelengths. Thus, a photoluminescent agent is an optically active agent of this kind. An agent for second harmonic generation is also an optically active agent in the sense of the present application. An example of such an agent for second harmonic generation is for example particles of KTP—standing for potassium titanyl phosphate (KTiOPO$_4$). In the rest of the description, the optically active second agent is a photoluminescent second agent. Unless stated otherwise, what is described for the photoluminescent second agent also applies in the case when this second agent is optically active, notably an agent for second harmonic generation.

The photoluminescent first agent comprises nanoparticles doped with rare earths.

Here, "nanoparticles" means particles whose diameter is of the order of a nanometer, notably greater than 1 nm and/or less than 500 nm. Here, "diameter" means the largest dimension of the nanoparticle.

In a preferred embodiment, the photoluminescent second agent also comprises nanoparticles doped with rare earths.

The photoluminescent first and second agents have different luminescence wavelengths. In other words, there is at least one first wavelength at which only the light emitted by the photoluminescent first agent is detectable and at least one second wavelength, different than the first, at which only the light emitted by the second agent can be detected. The photoluminescent agents are preferably selected in such a way that their line widths are small enough to be separated spectrally. This allows easier detection of the emissions from the photoluminescent first and second agents. To make this detection even easier and for greater accuracy, photoluminescent agents are selected whose maximum emission wavelengths are different and detection is performed at these maximum emission wavelengths.

Furthermore, the photoluminescent first agent is selected such that the intensity of its luminescence emitted at the detected wavelength (abbreviated hereinafter as: its luminescence) varies with the quantity of oxidizing species in whose presence it is. In the following, the case will be considered in which the luminous intensity of the luminescence of the photoluminescent first agent increases with the quantity of oxidizing species in whose presence it is.

The photoluminescent agents may be deposited so as to obtain a low surface density on or in a sample, which may for example be received on a glass slide. "Low surface density" means a surface density below 1 μm$^{-2}$.

However, the photoluminescent agent or agents considered in the methods according to the invention may also advantageously be introduced directly in a volumetric sample, for example a volume of liquid sample or in the bulk of a sample.

Photoluminescent First Agent

The photoluminescent first agent advantageously comprises nanoparticles of $A_x Eu_{1-x}(VO_4)_y(PO_4)_{(1-y)}$, where A is one from Y and Gd and La, 0≤x≤1 and 0≤y≤1.

In particular, in the following, the particular case is considered in which the photoluminescent first agent is formed by nanoparticles of $Gd_{0.6}Eu_{0.4}VO_4$.

According to a preferred variant, these nanoparticles are reduced, before being brought into contact with the analysis sample.

The reduced nanoparticles of a photoluminescent first agent of this kind may notably be obtained in a preliminary step 14 consisting of reducing nanoparticles to obtain the photoluminescent first agent.

As detailed hereinafter, reduction may be effected:
  physically, notably by laser, electronic or gamma irradiation, for example; or
  chemically, using a reducing chemical agent.

According to a first embodiment, before being brought into contact with the analysis sample, the nanoparticles of $A_x Eu_{1-x}(VO_4)_y(PO_4)_{(1-y)}$ are reduced physically, in particular by laser excitation.

In the context of this embodiment, the nanoparticles, when they are brought into contact with the analysis sample, already contain europium in the form $Eu^{2+}$. For example, in the case when particles of $Gd_{0.6}Eu_{0.4}VO_4$ are used, the $Eu^{3+}$ ions of the particles may be reduced reversibly to $Eu^{2+}$ ions in step 14 of the method of the invention.

It is to be understood that this reduced species of the nanoparticles of $A_x Eu_{1-x}(VO_4)_y(PO_4)_{(1-y)}$ may also be generated in situ, i.e. in the assay sample, for example by photoreduction of nanoparticles of $A_x Eu_{1-x}(VO_4)_y(PO_4)_{(1-y)}$ in which the species Eu is essentially in the form $Eu^{3-}$. This approach is notably described in Casanova et al., Nat Nanotech (2009).

However, the embodiment consisting of employing nanoparticles, of $Gd_{0.6}Eu_{0.4}VO_4$ for example, as the starting reactant, already incorporating Eu in the reduced form is preferred for its efficiency and simplicity. Moreover, this variant does not affect the integrity of any biological cells present in the assay sample.

According to another embodiment, before they are brought into contact with the analysis sample, the nanoparticles of $A_x Eu_{1-x}(VO_4)_y(PO_4)_{(1-y)}$ are reduced chemically, using a reducing agent.

This substep of chemical reduction may be followed by a further substep, consisting of washing the reduced nanoparticles, to remove excess reducing agent. For example, the particles are diluted in a solution containing a reducing agent, then centrifuged, and then dispersed again in fresh solution without a reducing agent (pure water for example), thus allowing successive washing operations.

The reducing agent employed may notably be NaBH$_4$. A last step may then consist of washing the reduced nanoparticles, to remove excess reducing agent.

For example, the nanoparticles of $Gd_{0.6}Eu_{0.4}VO_4$ may be reduced reversibly with sodium borohydride (NaBH$_4$) in step 14.

Figure 2:
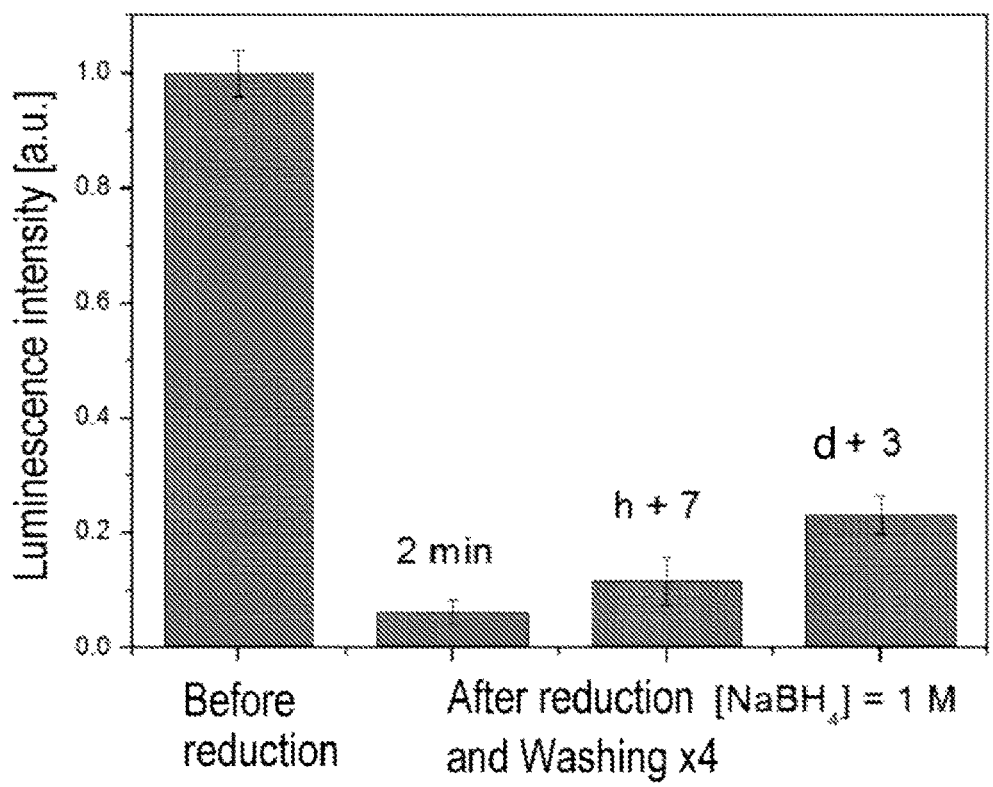
FIG. 2 shows the level of luminous intensity of the luminescence of nanoparticles of $Gd_{0.6}Eu_{0.4}VO_4$ after treatment with a solution of $NaBH_4$ (1 mol.l$^{-1}$)

FIG. 2 shows a comparison between the levels of luminescence of a solution of nanoparticles of $Gd_{0.6}Eu_{0.4}VO_4$ under laser illumination of wavelength 466 nm, before, immediately, 7 h and 2 days after treatment with 1M of NaBH$_4$.

The inventors have shown that the particles obtained following reduction with a chemical agent are capable of detecting oxidizing species, for example H$_2$O$_2$, in a similar fashion to the detection of H$_2$O$_2$ by particles with $Eu^{3+}$ ions reduced beforehand to $Eu^{2+}$ following laser excitation.

Thus, according to another of its aims, the invention relates to a method that can be used for analyzing oxidizing species in a sample, in particular in a biological sample, comprising the steps consisting of:
  i) providing photoluminescent nanoparticles of $A_x Eu_{1-x}(VO_4)_y(PO_4)_{(1-y)}$, where A is one from Y, Gd and La, 0≤x≤1 and 0≤y≤1, said nanoparticles being reduced beforehand, in particular chemically using a reducing agent, in particular by NaBH$_4$;
  ii) introducing said nanoparticles into the assay sample,
  iii) exciting said nanoparticles,
  iv) measuring the luminous intensity emitted by the sample at at least one wavelength representative of the oxidized form or of the reduced form of said nanoparticles, and iv) estimating the presence and/or the quantity of oxidizing species by interpreting said measurement, if applicable by reference to a standard or calibration.

It was not in any way obvious that reduction of the particles of $A_xEu_{1-x}(VO_4)_y(PO_4)_{(1-y)}$ with a chemical agent, for example $NaBH_4$, might give oxidizable nanoparticles capable of detecting oxidizing species, for example $H_2O_2$.

Without wishing to be bound to any theory, the inventors have shown that the mechanism of reduction is not the same in both cases.

In the case of reduction by laser excitation, the result of laser excitation resonant with the electronic transitions of the $Eu^{3-}$ ions is the appearance of $Eu^{2+}$ ions, which makes the particles oxidizable and capable of detecting oxidizing species. However, in the case of reduction of the nanoparticles by a chemical agent, there is no persistent significant change in the number of $Eu^{3+}$ ions, and reduction with a chemical agent probably involves a phenomenon of quenching acting on the emission of the $Eu^{3+}$ ions, with reoxidation of the particle allowing the return of luminescence.

Optically Active Second Agent

The optically active and preferably photoluminescent second agent is selected in such a way that its luminescence (or the luminous intensity of its luminescence) is constant or, preferably, also varies with the quantity of oxidizing species.

Thus, according to a first variant of the method for detecting oxidizing species 10 described above, the intensity of luminescence of the optically active, notably photoluminescent, second agent is roughly constant in the presence of oxidizing species.

"Roughly constant" means that the variation of luminous intensity is between plus or minus 10%, preferably plus or minus 5%. In this case, the optically active second agent may notably comprise or consist of nanoparticles of $LaPO_4$:Eu, $LaPO_4$:Er, $LaPO_4$:Nd, $LaPO_4$:Tb, $LaF_3$:RE (RE=rare earth), $NaYF_4$:Yb, $NaYF_4$:Er, YAG:Eu, fluorescent semiconducting nanocrystals CdSe/ZnS, CdTe/ZnS, or particles displaying properties of emission by second harmonic generation such as KTP and/or $BaTiO_3$. This variant of the method also makes it possible to detect the presence of oxidizing species in a test sample.

According to a second preferred variant of the method for detecting oxidizing species 10 described above, the intensity of luminescence of the optically active second agent varies as a function of the quantity of oxidizing species, in a direction opposite to the variation of luminescence observed at said first accredited length of the photoluminescent first agent.

Thus, in the rest of the description, it is considered that the luminescence of the photoluminescent second agent decreases with the quantity of oxidizing species, in whose presence it is. For example, the photoluminescent second agent may consist of a solution containing nanoparticles of YAG:Ce and/or $LaPO_4$:Ce. In the rest of the description, it is considered that the photoluminescent second agent is formed by nanoparticles of YAG:Ce.

Figure 3:
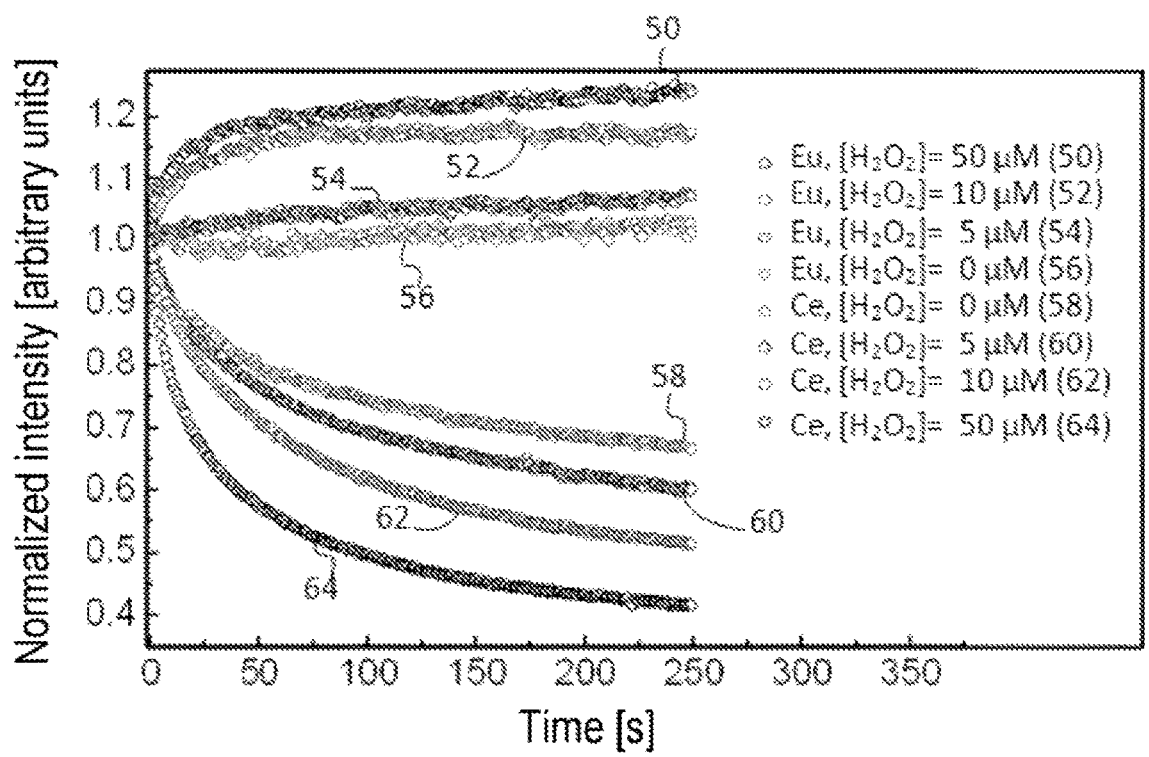
FIG. 3 shows intensity response curves of luminescence of reduced particles of $Gd_{0.6}Eu_{0.4}VO_4$ and of YAG:Ce, respectively, in oxidizing media with a known concentration of hydrogen peroxide.

FIG. 3 illustrates the emission intensity response curves 50-56 and 58-64 of the reduced particles of $Gd_{0.6}Eu0_{0.4}VO_4$ and of YAG:Ce, respectively, in an oxidizing medium with a known concentration of hydrogen peroxide, with a concentration equal to 0 µM, 5 µM, 10 µM and 50 µM, respectively. Each curve 50-64 is the average from monitoring about 10 nanoparticles detected individually.

Determination of the Presence or Absence of Oxidizing Species According to the Invention The method for determining the presence of oxidizing species 10 continues with a step 16, consisting of exciting the photoluminescent first and second agents in the sample. For this purpose, the sample may be subjected to double luminous excitation, notably by laser. In the case of the examples of photoluminescent agents considered in the present description, this double excitation of the sample may for example be performed at wavelengths of 396 nm (for $Gd_{0.6}Eu0_{0.4}VO_4$) and 488 nm (for YAG:Ce), by means of a laser diode and an argon laser, respectively.

The method for detecting oxidizing species 10 then continues with a step 18 consisting of measuring the luminous intensity emitted by the sample at at least one first wavelength corresponding to a luminescence wavelength of the photoluminescent first agent, and at at least one second wavelength, corresponding to a luminescence wavelength of the photoluminescent second agent, the first and second wavelengths being different. In the example considered here, the luminous intensity emitted by the sample is measured at the two luminescence wavelengths of $Eu^{3+}$ and $Ce^{3+}$, namely 617 nm and 550 nm, respectively.

In fact, the presence of oxidizing species in the sample causes, for example, oxidation of the $Eu^{2+}$ and $Ce^{3+}$ ions to $Eu^{3+}$ and $Ce^{4+}$ ions, respectively. This is reflected in a drop in the luminous intensity of emission of the particles based on cerium at a wavelength of 550 nm and an increase in the luminous intensity of the particles based on europium at a wavelength of 617 nm.

In the embodiment in which the second agent possesses a constant luminescence regardless of the concentration of oxidizing species to be analyzed, its accredited luminous signal may be used directly as a reference scale. Thus, this signal makes it possible to demonstrate either a change in the luminous intensity of the wavelength or of one of the wavelengths representative of the oxidized form or of the reduced form of the photoluminescent first agent, or a lack of variability of this intensity. A change in luminous intensity is representative of the presence of oxidizing species. Conversely, lack of variability of this luminous intensity indicates absence of oxidizing species in the sample to be analyzed.

In another embodiment, the method comprises a step 20 of comparison of the measured luminous intensities, at the scale of the individual nanoparticle, of the luminescence of each of the photoluminescent agents against standard values, in order to determine the quantity of oxidizing species in the sample tested. This step is notably necessary in the case when the luminous intensity of the photoluminescent second agent also varies with the quantity of oxidizing species in the analysis sample. The quantity of oxidizing species may notably be a concentration of oxidizing species in the sample tested.

Figure 4:
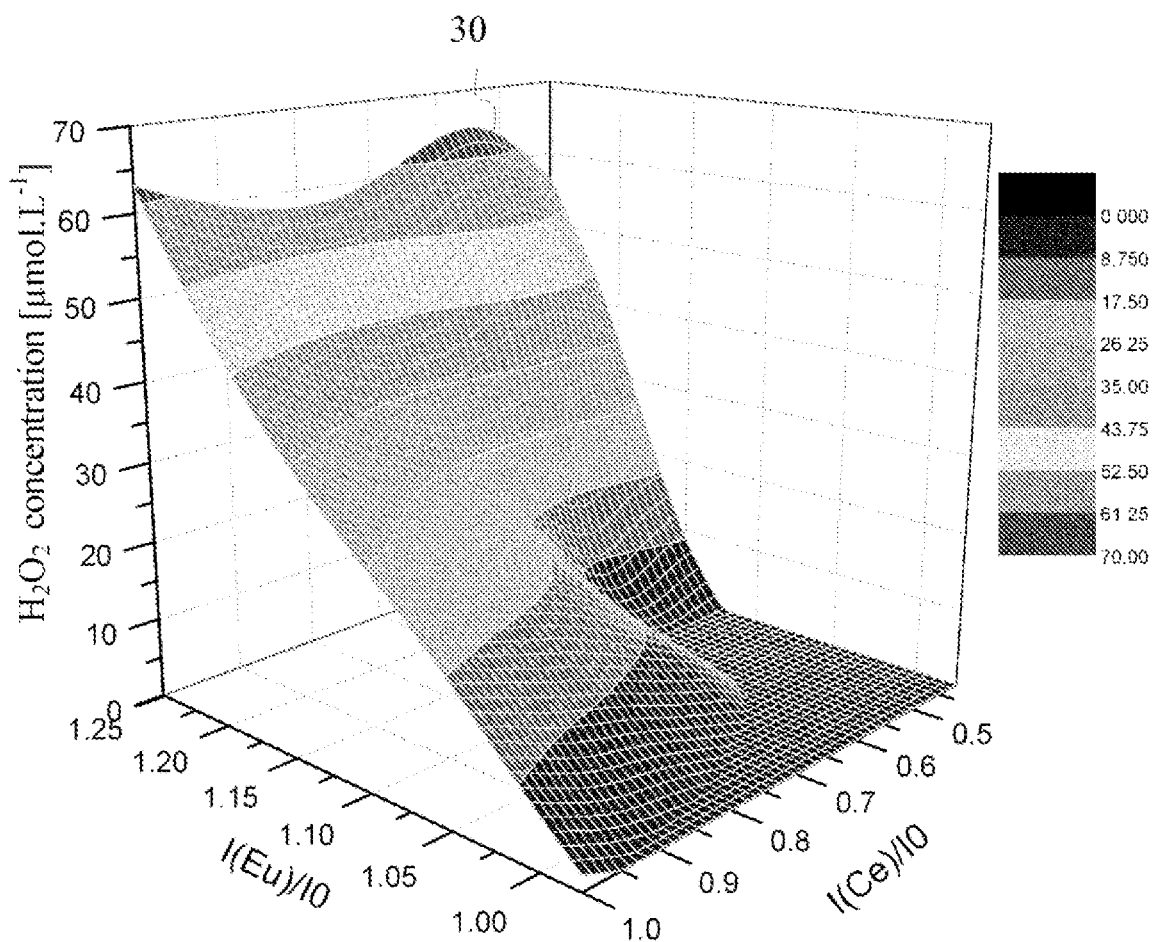
FIG. 4 shows an example of a sheet indicating a concentration of hydrogen peroxide in a sample as a function of a pair of measured luminous intensities.

Here, the standard values may be determined from a sheet 30 as illustrated in FIG. 4. This sheet represents a set of points corresponding to a triplet:
  luminous intensity of the luminescence of the photoluminescent agent comprising the particles based on europium,
  luminous intensity of the luminescence of the photoluminescent agent comprising the particles based on cerium, and
  concentration of oxidizing species ($H_2O_2$ in the case shown in FIG. 3).

This sheet 30 may notably be obtained at least partially starting from curves 50-64 in FIG. 3. Here, in fact, as the two photoluminescent agents have an opposite luminescence response as a function of the quantity of oxidizing species, each pair of curves 50-64 corresponding to one and the same concentration of oxidizing species makes it possible to determine a point of the sheet 30. As a variant, sheet 30 may be interpolated based on the data set of curves 50-64 where a pair of normalized luminous intensities corresponds uniquely to a concentration of oxidizing species.

Thus, advantageously, in the case of different, monotonic dependences of the luminescences of the two agents with the concentration of oxidants, it is possible to construct a sheet uniquely determining a concentration of oxidant based on the instantaneous luminescences of the two agents. Several types of luminescence response may be envisaged for the two agents. However, a preferred variant is the use of two agents having variations of luminescence with opposite response to the oxidants.

As a variant of this sheet 30, the standard values may be obtained from a table or from computer software, which may also interpolate, from measured points, a concentration of oxidizing species, of a pair of measured intensities.

In all cases, this comparison of the pair of measured luminous intensities against standard values makes it possible to dispense with measurement of the derivative of the luminous intensities, which is necessary for the method described in Casanova et al., Nat. Nanotech (2009). The method thus offers better temporal resolution.

The luminous intensity measured at the luminescence wavelengths of the $Eu^{3+}$ and $Ce^{3+}$ ions therefore makes it possible to determine a point of the sheet 30 corresponding to a unique concentration of oxidizing species present in the sample tested. The uniqueness of this concentration is ensured by the different, monotonic variations of the luminescence intensity of the photoluminescent agents as a function of the quantity of oxidizing species with which they are present.

The method for detecting oxidizing species according to the invention is therefore particularly advantageous for determining quickly, and relatively simply, a quantity of oxidizing species in a sample from a double measurement of luminous intensity.

This method allows a ratiometric measurement. Notably, in the case when the luminescence of the photoluminescent first agent varies as a function of the quantity of oxidizing species, but the luminous intensity emitted by the optically active second agent is roughly constant regardless of the concentration of oxidizing species, it may be advantageous to use the ratio between the intensities of emission of the first and second agents for determining the concentration of oxidizing species.

The method is, moreover, particularly suitable for detecting reactive oxygen species (or ROS) in the bulk. In fact, such detection depends neither on the concentration of photoluminescent agents, nor on the volume of the sample probed. The method may notably be employed for monitoring the production of oxidizing species in living tissues (sampled ex vivo or in vivo).

It will be recalled that the ROS are known to be produced abnormally in pathologies such as certain cancers, neurodegenerative diseases and cardiovascular diseases. The method described may therefore complement the numerous studies conducted in this field and thus help to respond to the public health challenges posed by these pathologies.

The method proposed is also advantageously adaptable to variable concentrations of oxidizing species, notably by modifying the luminous intensity of excitation of the photoluminescent agents. The oxidizing species that can be detected using the method include notably, but not exclusively, $H_2O_2$, NO and ClO. The method makes it possible to determine an absolute concentration of oxidizing species in the sample. It offers better spatial and temporal resolution than the known methods. It does not cause any side effects, and is biocompatible. It may be used for assaying oxidizing species in cells or biological tissues, but also for detecting and/or assaying oxidizing species in a solution of biological molecules.

The method 10, described above, may notably be implemented by means of a system 100 for determining the presence of oxidizing species as illustrated in FIG. 1. In FIG. 1, the system for determining the presence of oxidizing species in a sample 102 comprises firstly a laser illumination device 104 formed here from two different laser sources 106, 108, configured to emit beams at different wavelengths. In the example considered above in which the photoluminescent agents are $Gd_{0.6}Eu0_{0.4}VO_4$ and YAG:Ce, the first laser source 106 is configured to emit a first laser beam 110 at a wavelength of 488 nm, whereas the second laser source 18 emits a second laser beam 112 with a wavelength of 396 nm.

The system 100 next comprises a dichroic mirror 114 for combining the first and second laser beams 110, 112, and guiding them toward an optical lens 116 for focusing the laser beams 110, 112 on a zone of the test sample 102. This zone may for example correspond to an area of some $mm^2$. It should be noted here that the sample 102 may be arranged on or in a sample holder 103. Notably, in the case when the sample is gaseous, this sample holder 103 takes the form of a closed space to prevent dispersion of the test sample 102. The sample holder 103 may also take the form of a cell or cuvette, in particular in the case when the sample 102 is in the form of solution.

Figure 5:
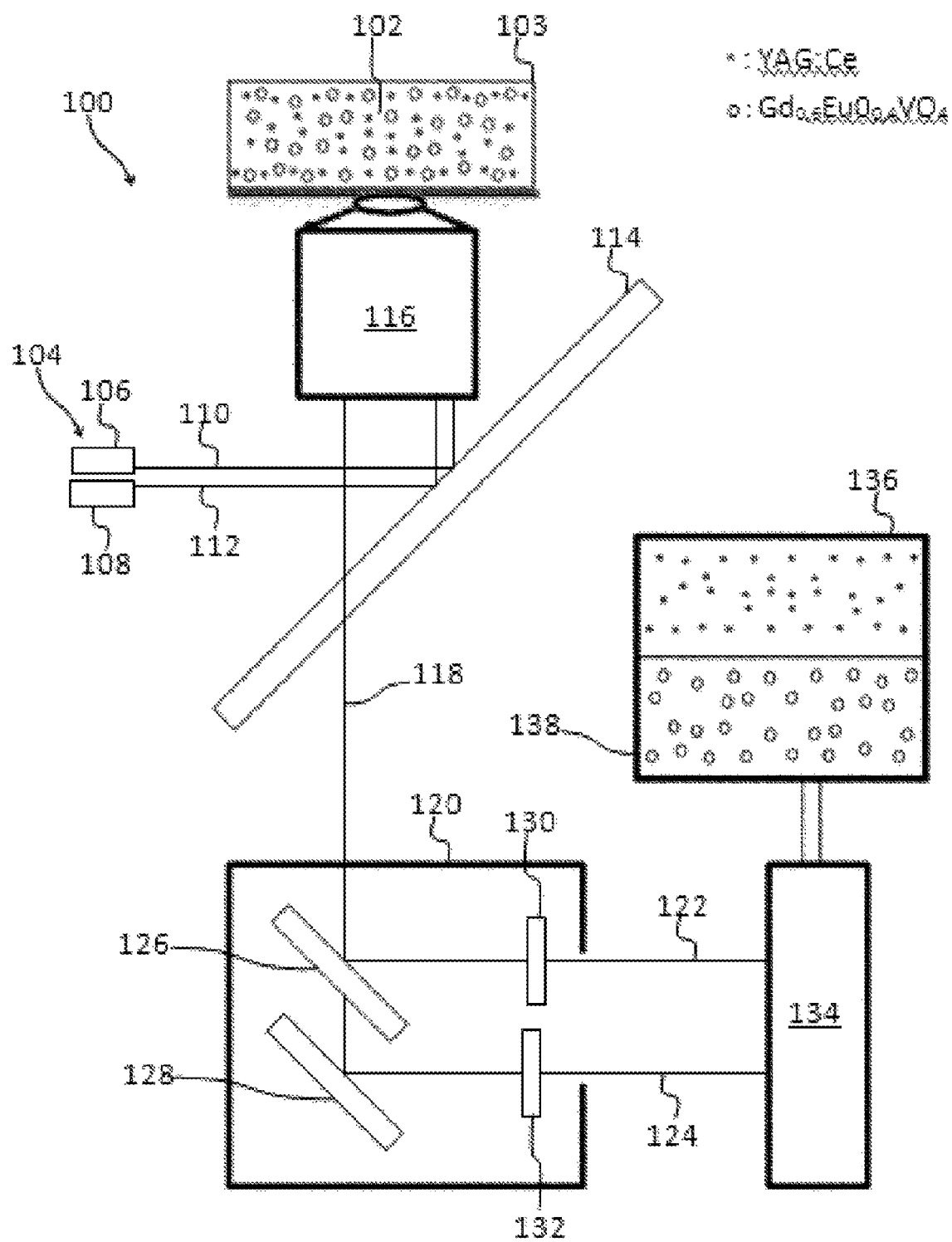
FIG. 5 is a schematic representation of a system for implementing the method shown in FIG. 1.

The test sample is brought into contact with the photoluminescent first agent and the optically active second agent, here photoluminescent. As in the example considered previously, the photoluminescent agents in this case take the form of two different types of particles:

particles of YAG:Ce (designated "*" in FIG. 5), and
reduced particles of $Gd_{0.6}EuO_{0.4}VO_4$ (designated "o" in FIG. 5).

The first and second laser beams 110, 112 excite the photoluminescent first and second agents in the sample 102. The photoluminescent agents, of different types, respond to the excitation of one of the two laser beams, preferably selectively (i.e. exclusively to one or the other), by emitting in two different wavelength ranges. "Two different wavelength ranges" means two ranges of wavelengths comprising at least one wavelength not included in the other wavelength range. For example, here, the particles of YAG:Ce respond to the excitation of the first laser beam at 488 nm, by emitting at a first wavelength of 550 nm. The reduced particles of $Gd_{0.6}EuO_{0.4}VO_4$ respond to the excitation of the second laser beam at 396 nm by emitting at a second wavelength of 617 nm.

The lens 116 makes it possible to focus the emission of the two luminescent agents 118 including the two response wavelengths of the photoluminescent agents onto a spectrum splitter 120, optionally via the dichroic mirror 114 through which it passes. The dichroic filter 114 then performs the role of a separating plate functionally interposed between the laser sources 106, 108 and the sample 102, on the one hand, and between the sample 102 and the spectrum splitter 120, on the other hand, by reflecting the laser sources and by being transparent to the emission of the luminescent agents.

As a variant, the lens is incorporated in an optical device, notably a microscope, functionally interposed between the sample 102 and the spectrum splitter 120. This microscope may notably be a, preferably wide-field, fluorescence microscope, a macroscope or a stereomicroscope.

The spectrum splitter 120 makes it possible to obtain, from a single incoming beam 118, two output images 122, 124 filtered at two different wavelengths, here the response wavelengths of the photoluminescent agents in contact with the sample 102. In other words, the spectrum splitter 120 makes it possible to filter the emissions of the photoluminescent agents according to different wavelengths and thus form two separate filtered images of the test sample 102.

For this purpose, the spectrum splitter 120 in this case comprises a dichroic mirror 126. First 130 and second 132 filters of respective wavelength corresponding to the response wavelengths of the photoluminescent agents are placed respectively in the path of 20 the beam 122 reflected by the dichroic mirror 126 and in the path of the beam 124 passing through the dichroic mirror 128. This allows spatial separation of the beams of different wavelengths for detection on two separate sensors or on two different regions of a single sensor, such as a camera 134.

The system 100 further comprises means for determining the luminous intensity associated with the two filtered images. Here, these means comprise a camera 134, for example an EMCCD camera (EMCCD: Electron Multiplying Charge Coupled Device) connected to a recorder, for example a computer, for detecting the two filtered images, each on a respective region 136, 138, corresponding to the response of each of the two photoluminescent agents.

Alternatively, the means employed for determining the luminous intensity comprise two photodetectors at different wavelengths, notably of the photomultiplier or photodiode type. These photodetectors make it possible to measure the total luminous intensity arriving from the whole of the illuminated sample without spatial resolution.

It should be noted here that the system 100 makes it possible to detect particles of each type simultaneously and individually. In the case when a full-field device is used, such as the camera 134, the particles may moreover be detected individually and localized spatially, because of the low surface density of the sample. Thus, monitoring at the scale of each single particle, of these two luminescence emissions and of their variations allows quantitative, local (notably with a localization precision of 40 nm) and time-resolved measurement, with an acquisition rate of the order of 100 ms, notably 33 ms, of the oxidizing species in the sample. The temporal resolution of the measurement is in fact then given by the acquisition rate of the camera 134.

The powers of the excitation lasers may, moreover, be modulated to change the range of concentrations of oxidizing species detected. The method and the system for detecting oxidizing species may thus notably be employed in many applications, such as detection of ROS in inflammations or certain tumors.

EXAMPLES

Example 1

An example of an experiment conducted for detecting oxidizing species produced in a mammalian cell following stimulation by a protein is described in detail below.

Firstly, mammalian cells were prepared. For this purpose, mouse vascular smooth muscle cells (primary culture) were cultured in RPMI ("Roswell Park Memorial Institute" medium) containing 10% of fetal calf serum and antibiotics, in the present case penicillin and streptomycin. When confluence reaches 80%, the cells are taken and deposited on glass slides. In this particular case, $1.5 \times 10^4$ cells are typically arranged on a glass slide. The cells are then cultured on the slides for forty-eight hours in the complete culture medium, and then in a medium without serum for twenty-four hours.

In addition, a stable colloidal solution of $Gd_{0.4}EuO_{0.6}VO_4$ with a concentration roughly equal to 1 mM is prepared. The solution is then centrifuged for five minutes at an acceleration of 5000 g in order to precipitate the particles. The supernatant is removed and the pellet is resuspended in an aqueous solution of sodium borohydride ($NaBH_4$) of concentration 1 M. Reaction of the $NaBH_4$ with the particles and with water produces dihydrogen in the form of bubbles. Therefore care is taken not to confine the reaction mixture. After some minutes, the solution is centrifuged again, for five minutes, at an acceleration of 5000 g. The supernatant is removed and the pellet is resuspended in distilled water. The washing operation is repeated twice in order to remove any residual reducing ions.

A stable solution of YAG:Ce (4%) of about 1 mM is prepared, with water as the main solvent. These particles are synthesized by the glycothermal route in the form of dispersions in ethanol. Washing cycles are carried out: the necessary centrifugations may be effected for 5 minutes at an acceleration of 5000 g and then the particles are resuspended in the solvent selected for the measurements, water in the case described here.

In addition, 10 μL of suspension of YAG:Ce and 15 μL of suspension of reduced and washed particles of $Gd_{0.4}EuO_{0.6}VO_4$ are mixed in a commercial solution of hypertonic medium (LifeTechnologies). The cells are incubated with this solution for ten minutes and then two minutes in a hypotonic solution containing 70% of RPMI and 30% of sterile distilled water. Then the cells are incubated in their complete medium for thirty to sixty minutes.

Figure 6:
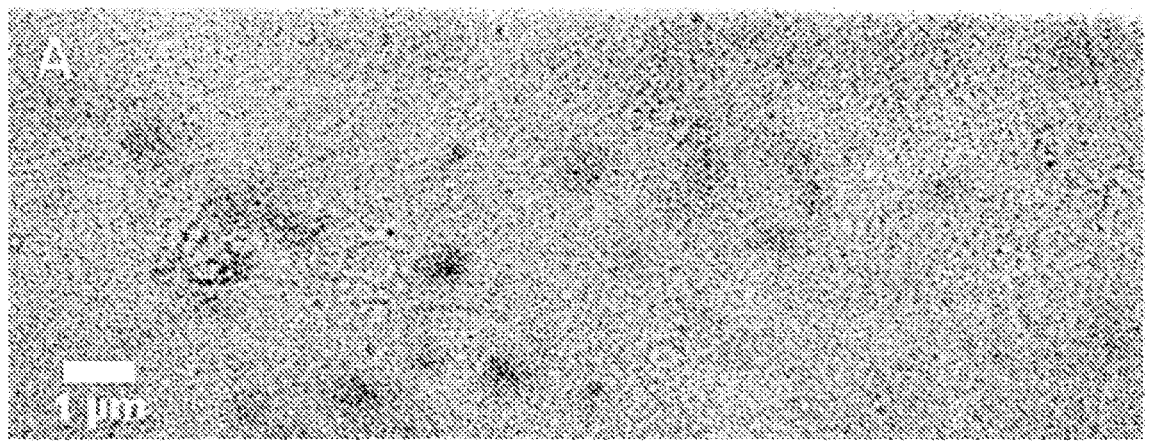
FIG. 6 shows an example of observation of a sample, according to example 1, of mouse vascular smooth muscle cells in culture, under white light.
Figure 7:
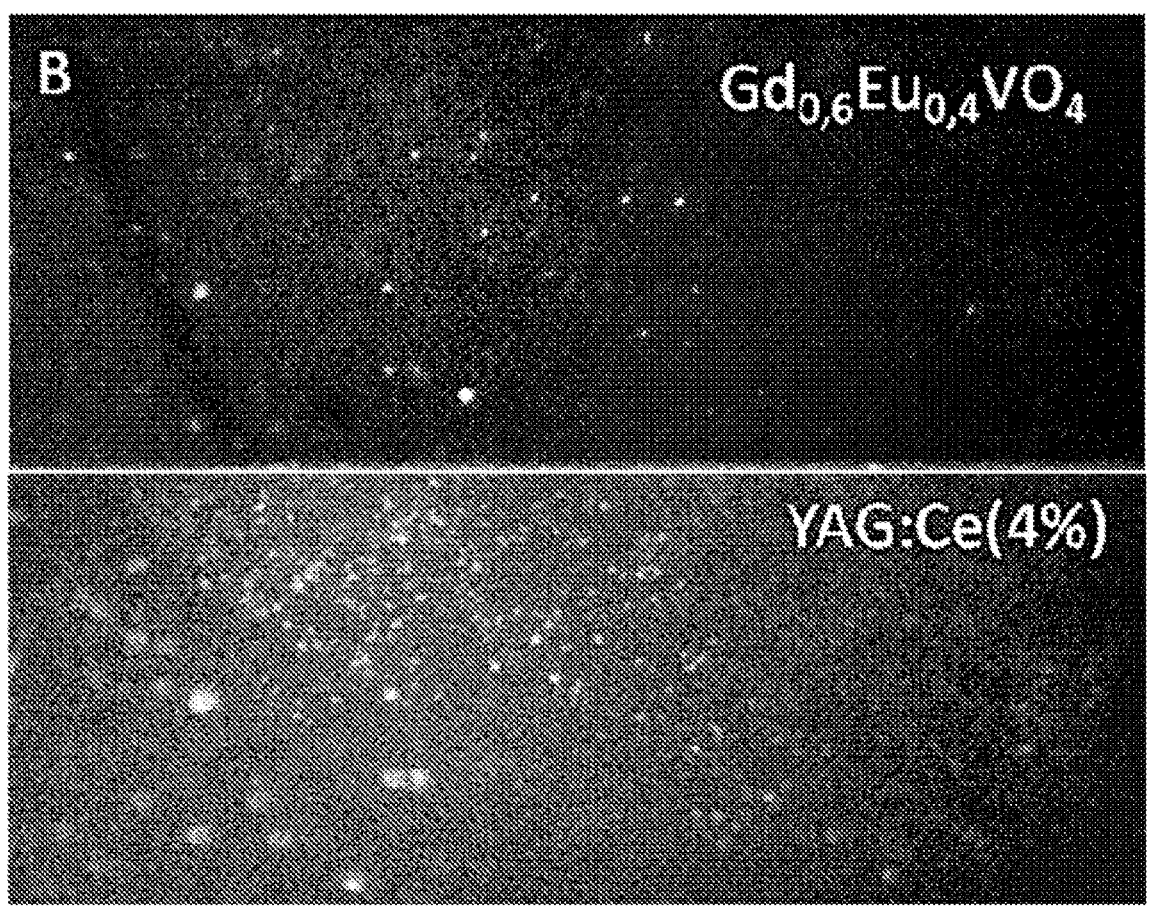
FIG. 7 shows an example of observation of the same sample, according to example 1, in which the nanoparticles indicated in the figure have been internalized and their luminescence is detected at wavelengths of 550 nm and 617 nm.
Figure 8:
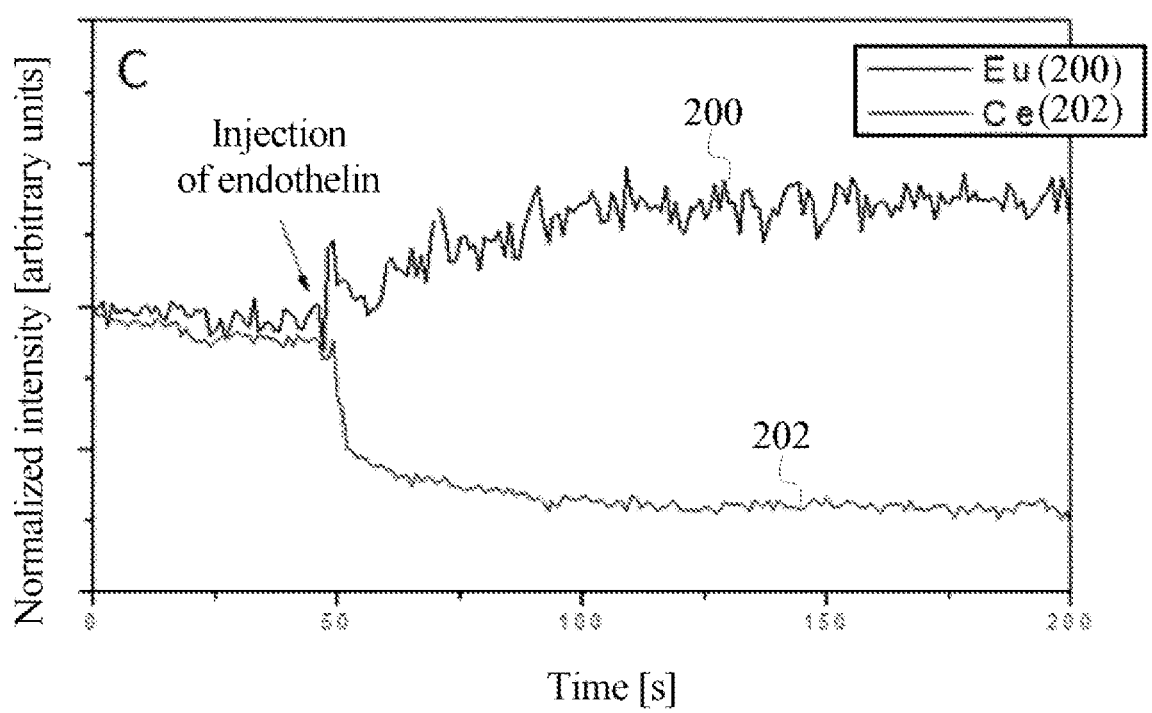
FIG. 8 shows the variation over time of the luminous intensity of photoluminescent agents in contact with the sample in FIG. 6 after injection of endothelin, according to example 1.

Then a slide with cells loaded with nanoparticles is placed on a sample holder and 1 mL of buffered physiological medium (HBSS/1 mM HEPES) is added. The slide is then mounted on an epifluorescence microscope for observation of individual particles (Olympus IX71, Objective x63 NA=1.4). Then the cells are observed in transmission of white light, as illustrated in FIG. 6, and under dual illumination (laser sources at 488 nm and 396 nm), as illustrated in FIG. 7. A cell having a suitable morphology is selected, i.e. a cell that is alive and adherent. After fifty seconds of observation, the initial medium is replaced with physiological medium containing 270 nM of endothelin-1 (ET-1) and the luminescence of individual nanoparticles is observed for several minutes on a full-field sensor (EM-CCD ImageEM camera, Hamamatsu). FIG. 8 illustrates the response curves 200, 202 corresponding to the particles based on Eu and Ce, respectively. We observe an increase in luminous intensity of the particles based on Eu and a decrease in luminous intensity of the particles based on Ce.

Figure 9:
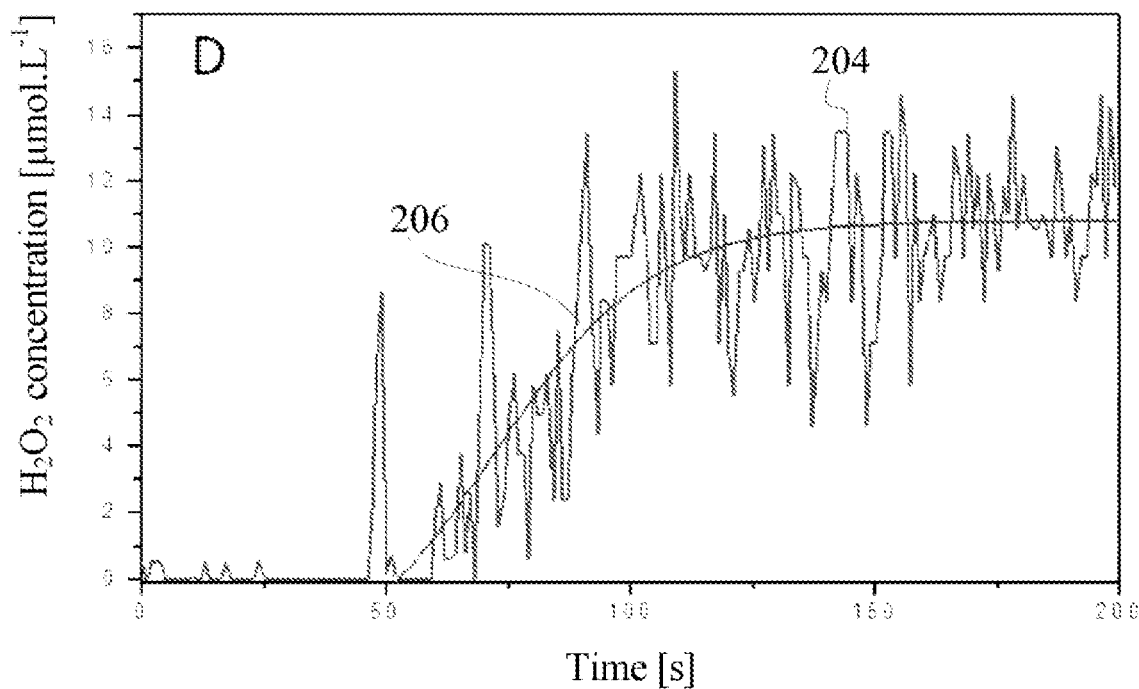
FIG. 9 shows the concentration of hydrogen peroxide in the sample in FIG. 6 obtained according to example 1, after injection of endothelin, determined from the sheet presented in FIG. 4.

Next, the variations in intensity of the particles observed (doped with Ce or Eu) over time are determined using image analysis or calculation software (for example Matlab). Each curve obtained is normalized, taking the first values measured for reference. The concentrations of hydrogen peroxide are found from the sheet 30 in FIG. 4. The curve 204 illustrated in FIG. 9 is thus obtained, as well as the corresponding smoothed curve 206, which gives the variation of the concentration of $H_2O_2$ in the sample tested, as a function of time.

Example 2

Figure 10:
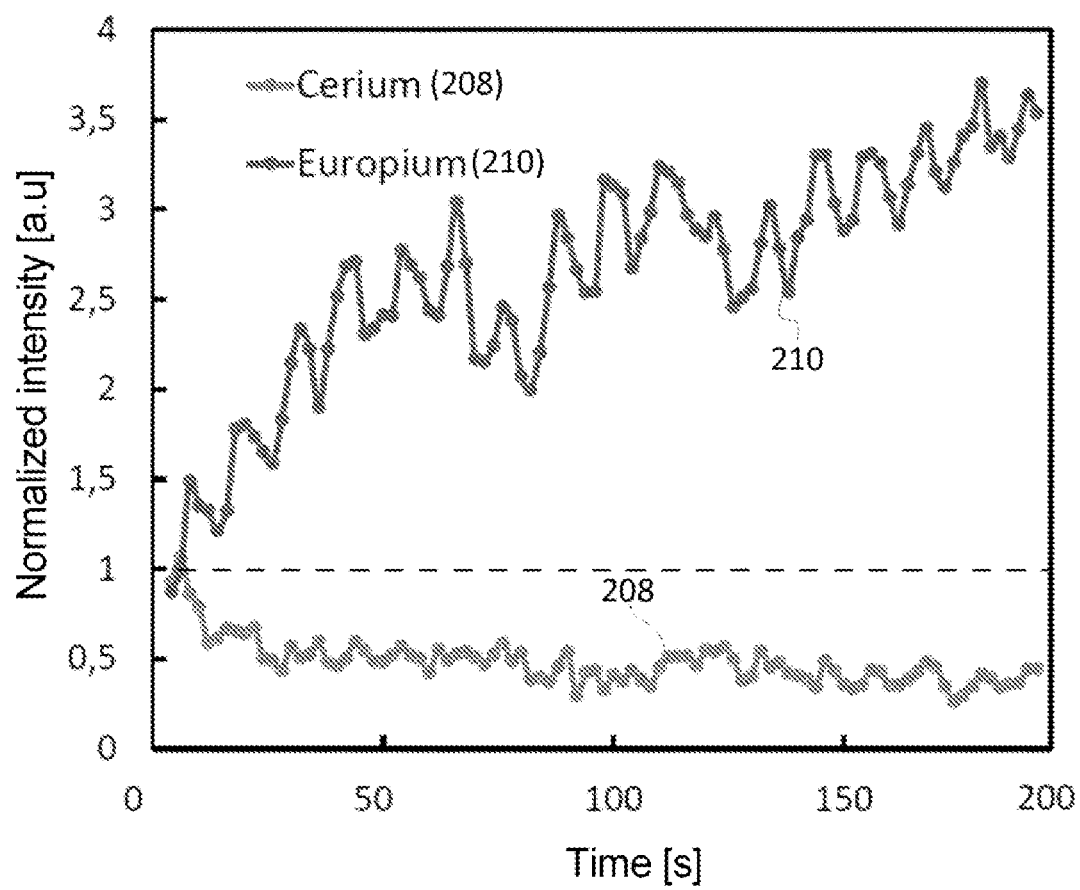
FIG. 10 shows the variation of the luminescence of a solution in a vessel, according to example 2, containing a mixture of particles YAG:Ce and $GdVO_4$:Eu after adding 2 mM of hydrogen peroxide (at t=0), detected at 550 nm and 617 nm on two photomultipliers.

FIG. 10 illustrates another example of use of the method according to the invention, in which the sample to be analyzed is contained in a vessel. The two agents, YAG:Ce and $GdVO_4$:Eu respectively, are put in the vessel in solution. They are excited by specific sources. After adding 2 mM of hydrogen peroxide (at t=0), the luminescence of each of the agents, detected at 550 nm and 617 nm, is collected on two photomultipliers, to form the two curves 208, 210, respectively.

Example 3

The vascular smooth muscle cells coat the walls of blood vessels. Stimulation of them by a powerful vasoconstrictor such as endothelin-1 (ET-1) causes them to contract and induces an increase in arterial pressure. The cell signaling process responsible for this response is known to induce production of hydrogen peroxide (oxidizing species). Moreover, the membrane receptors EGFR (Epidermal Growth Factor Receptor) are also known to participate in this process. However, their contribution and in particular their effect on the production of oxidants are still unknown. This is because there are no methods for quantitative detection that are fast enough for characterizing this phenomenon.

In this example, the transactivation of the EGFR receptors in response to the vasoconstrictor ET-1 was studied by the method of the invention.

For this, the same protocol as in example 1 was followed, namely culture of vascular smooth muscle cells, preparation of the suspension of reduced particles YAG:Ce and $Gd_{0.4}Eu_{0.6}VO_4$, and incubation of the cultured cells with the suspension.

Figure 11:
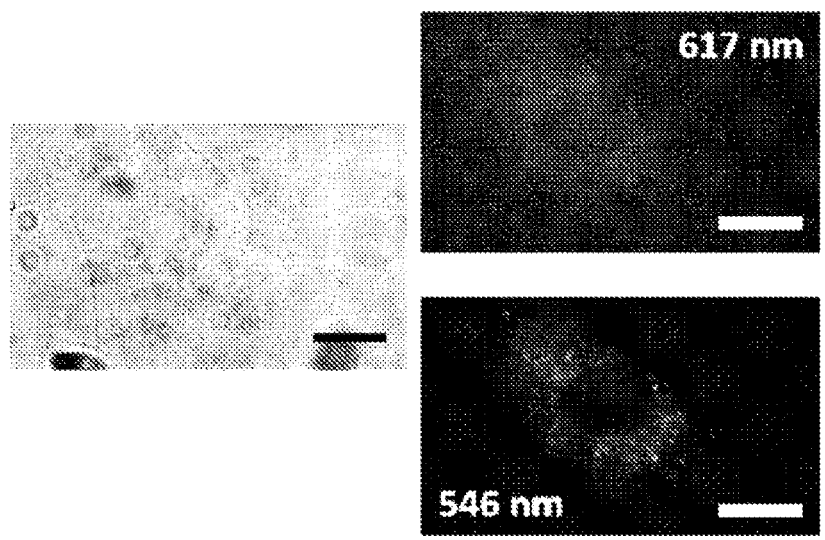
FIG. 11 shows the photographs obtained by fluorescence microscopy and spectrum splitting of a sample according to example 3 of mouse vascular smooth muscle cells in culture.

The presence of these particles was observed by fluorescence microscopy and spectrum splitting, as indicated in example 1 (FIG. 11). A mixture of nanoparticles ($GdVO_4$:Eu reduced chemically beforehand and YAG:Ce) is internalized in vascular smooth muscle cells deposited on a glass slide (170 µm) and the slide is mounted on an epifluorescence microscope for observation of individual particles (Olympus IX71, Objective x63 NA=1.4) equipped with a spectrum splitter allowing the photoluminescence of each type of particle to be projected on two different regions of an ultra-sensitive camera (EM-CCD, Evolve 512 Roper Scientific).

Figure 12:
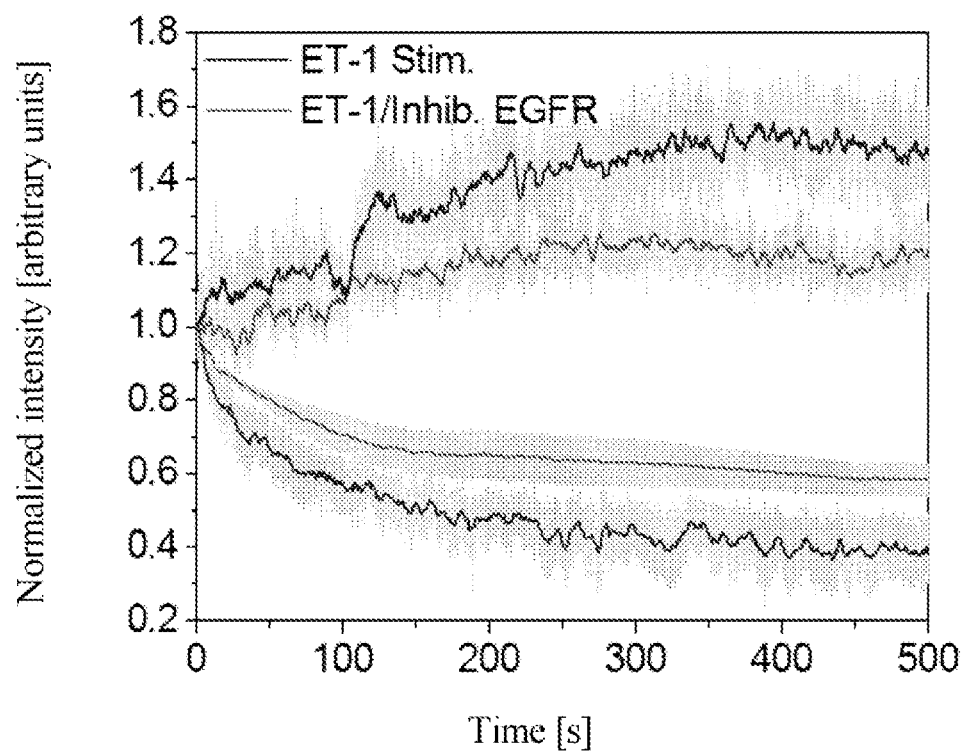
FIG. 12 shows the variation, according to example 3, of the photoluminescences normalized by their initial value of the nanoparticles YAG:Ce (below 1) and $GdVO_4$:Eu (above 1) obtained after stimulation by ET-1, with or without inhibition of the EGFRs.

The stimulation of normal cells and of cells where the EGFRs have specifically been inhibited by the presence of the agent AG1478 (application 30 min before stimulation and addition to the medium for observation under the microscope) was performed with a concentration of 270 nM of endothelin-1. Immediately after stimulation, the luminescence signals emitted by the different particles in the cells were collected. Thus, FIG. 12 shows the photoluminescences normalized by their initial value of the nanoparticles YAG:Ce (below 1) and $GdVO_4$:Eu (above 1) obtained after stimulation by ET-1 (with or without inhibition of the EGFRs).

Figure 13:
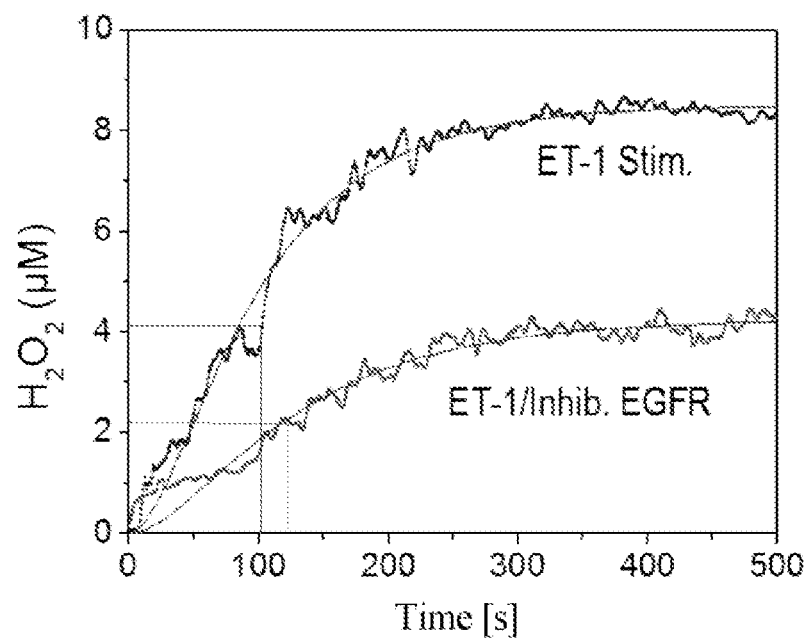
FIG. 13 shows the temporal variation of the absolute concentrations of hydrogen peroxide in the two cellular conditions (normal or EGFR inhibited) determined according to example 3.

Next, owing to calibration as described above, the temporal variation of the absolute concentrations of hydrogen peroxide was deduced (FIG. 13) in the two cellular conditions (normal or EGFRs inhibited). This step makes it possible to quantify the contribution of the EGFR pathway to the overall signaling process. This contribution reaches 50%, since the inhibited cells produce half as much hydrogen peroxide as the normal cells. It also makes it possible to quantify the effect of this inhibition on the kinetics of production of hydrogen peroxide, in contrast for example to Bouzigues et al., Chem. Biol., 2014; 21:647-56, by revealing that the transactivation of the EGRs takes place in less than 1 second and controls said kinetics of production to times <1 min.

Of course, the present invention is not limited to just the examples described above; many variants are accessible by a person skilled in the art, within the scope of the accompanying claims.

Thus, for example, the optically active second agent may consist of any type of photostable agent, such as semiconducting nanocrystals, for example.

Moreover, the particles may be functionalized and coupled to one or more biomolecules of interest notably for the purpose of targeting either specific cellular compartments in the case of measurements at the cellular level, or specific cell types, for example cancer cells, in the case of measurements at the level of tissues or in vivo (in living organisms).

More precisely, the biologically active molecules are targeting molecules, i.e. molecules that will allow specific targeting of the particle according to the invention to an organ, a body fluid (for example blood), a cellular type (for example platelets, lymphocytes, monocytes, tumor cells, etc.) or a cellular compartment. Thus, this specific targeting may be accomplished using monoclonal or polyclonal antibodies, or protein or polypeptide ligands of cellular receptors. As nonlimiting examples, we may mention the following receptor/ligand pairs: TGF/TGFR, EGF/EGFR, TNFα/TNFR, interferon/interferon receptor, interleukin/interleukin receptor, GMCSF/GMCSF receptor, MSCF/MSCF receptor, and GCSF/GCSF receptor. We may also mention, as ligands, toxin fragments or detoxified toxins and their cellular receptors. Regarding the antibodies, they will be selected as a function of the antigen or antigens against which the antibody is directed.

In another embodiment, the biologically active molecule or molecules are stealth agents, such as polyethylene glycol (PEG) or dextran, for endowing the particles with stealth characteristics in the body and thus increasing their circulation time in the blood.

In a particular embodiment, the particles according to the invention may be functionalized with targeting molecules and stealth molecules as defined above.

Regardless of the embodiment, the biologically active molecules may be attached to the surface of the particle or if applicable to the preparation layer, directly or via a layer bearing functional groups, by covalent or noncovalent bonds. Attachment of these biologically active molecules is performed by the conventional techniques of oxidation, halogenation, alkylation, acylation, addition, substitution or amidation of the surface of the particle, of the preparation layer and/or of the layer bearing functional groups, with the biologically active molecules.

The preparation layer is applied directly on the particle, either by covalent binding or by absorption. This preparation layer may be hydrophilic or hydrophobic. In a particular embodiment, this preparation layer is amorphous.

Coupling between the particles and a biomolecule is described for example in application WO-A-2012/010811. Furthermore, application WO-A-2013/123197 describes coating of the particles, which may lead to particles coupled to biomolecules.

Moreover, in order to improve the signal to noise ratio, it is possible to use delayed detection of the signal emitted by the europium-doped particles, which have a long lifetime of the excited state compared to most fluorophores. With the aid of a device for occultation, notably mechanical or electronic, of the means for determining the luminous intensity, selectively activatable, this approach consists of detecting, after a laser pulse for excitation of the first and second agents, only the photons emitted after a set time. This set time may be selected so as not to detect the photons coming from other emitters, for example by autofluorescence, and only detect photons emitted by the $YVO_4$:Eu nanoparticles.

The invention claimed is:

1. A method of detecting oxidizing species, said detecting method comprising a step of analyzing a sample of oxidizing species, said analyzing step consisting of:
   i) contacting the sample with a photoluminescent first agent and an optically active second agent, the photoluminescent first agent at least comprising nanoparticles doped with rare earths and oxidizable, with
      the luminescence of the photoluminescent first agent varying, at at least one first wavelength, with the quantity of oxidizing species, and
      the signal emitted by the optically active second agent being, at at least one second wavelength different from the first wavelength,
         constant with the quantity of oxidizing species, or
         varying with the quantity of oxidizing species in a direction opposite to the luminescence of the photoluminescent first agent,
   ii) exciting the photoluminescent first agent and the optically active second agent in the sample;
   iii) measuring the luminous intensity of the sample at at least said first wavelength, and at least said second wavelength; and
   iv) estimating the presence and/or the quantity of oxidizing species by interpretation of said measured luminous intensities, and if applicable by reference to standard values.

2. The method as claimed in claim 1, where in step iv) of the analysing step, a quantity of oxidizing species in the sample is determined by reading, on a standard sheet, the value corresponding to the pair of luminous intensities measured in step iii), wherein the standard sheet is a reference sheet produced from a set of points that are determined through calibration in a three-dimensional graphic, each point corresponding to a triplet, wherein the three dimensions are:
   luminous intensity of the luminescence of the first photoluminescent agent;
   luminous intensity of the signal emitted by the optically active second agent; and
   concentration of oxidizing species.

3. The method step as claimed in claim 2, in which the standard sheet is established beforehand by means of measurements performed with samples with a known quantity of oxidizing species.

4. The method as claimed in claim 1, in which step iii) of the analysing step is performed after a nonzero set waiting time after step ii).

5. The method as claimed in claim 1, where in the analysing step the luminous intensity of the luminescence of the photoluminescent first agent increases with the quantity of oxidizing species.

6. The method as claimed in claim 1, where in the analysing step the luminous intensity of emission of the optically active second agent is roughly constant with the quantity of oxidizing species.

7. The method as claimed in claim 1, where in the analysing step the optically active second agent is photoluminescent.

8. The analyzing step as claimed in claim 7, in which the optically active second agent comprises nanoparticles of $LaPO_4$:Eu, $LaPO_4$:Er, $LaPO_4$:Nd, $LaPO_4$:Tb, $LaF_3$:RE, $NaYF_4$:Yb, $NaYF_4$:Er, CdSe/ZnS, CdTe/ZnS, KTP and/or $BaTiO_3$, wherein RE represents rare earth.

9. method as claimed in claim 1, where in the analysing step the luminous intensity of emission of the optically active second agent decreases with the quantity of oxidizing species.

10. The method as claimed in claim 1, where in analysing step the first wavelength is representative of the oxidized form of the photoluminescent first agent and the second wavelength is representative of the reduced form of the optically active agent.

11. The method as claimed in claim 1, where in the analysing step the photoluminescent first agent comprises at least partially reduced nanoparticles of $A_xEu_{1-x}(VO_4)_y$ $(PO_4)_{(1-y)}$, where A is one from Y, Gd and La, $0 \le x \le 1$ and $0 \le y \le 1$.

12. The method as claimed in claim 11, comprising a step a), prior to step i), consisting of reducing nanoparticles to obtain the photoluminescent first agent.

13. The method as claimed in claim 12, in which, in step a), reduction is performed chemically, using a reducing agent.

14. The method as claimed in claim 13, in which the reducing agent contains $NaBH_4$.

15. The analyzing step as claimed in claim 13, in which step a) comprises a substep, subsequent to the chemical reduction, consisting of washing the reduced nanoparticles to remove the excess reducing agent.

16. The method as claimed in claim 1, where in the analysing step the particles are additionally coupled to one or more functionalized biomolecules and/or biomolecules known to be of interest selected from targeting molecules and stealth agents.

17. The method as claimed in claim 1, where in the analysing step the sample is one from:
   a living organism;
   biological tissues;
   biological cells;
   a solution of biological molecules;
   a volume of gas.

18. The method as claimed in claim 1, where in the analysing step the sample is a biological sample, wherein the presence and/or the quantity of oxidizing species provides a diagnosis of a disorder associated with expression of said oxidizing species.

19. The method as claimed in claim 18, wherein the disorder is a physiological disorder, whether or not pathological, and associated with expression of one or more reactive oxygen species (ROS) that is not physiologically acceptable.

20. The method as claimed in claim 18, wherein the biological sample is a volumetric sample.

21. The analyzing step as claimed in claim 1, where in the analysing step the sample is a biological sample obtained from a patient treated with a therapeutic active substance, wherein the presence and/or quantity of oxidizing species in the sample is compared to the presence and/or quantity of oxidizing species in a biological sample obtained from the patient prior to treatment with the therapeutic active substance to provide an indication as to the efficacy of the active substance with respect to a disorder associated with overexpression of one or more reactive oxygen species (ROS).

22. The method as claimed in claim 21, wherein the biological sample is a volumetric sample.

23. The analyzing step as claimed in claim 1, in which in the analysing step the optically active second agent comprises nanoparticles of YAG:Ce, LaPO$_4$:Ce.

24. The analyzing step as claimed in claim 1, in which in the analysing step the photoluminescent first agent comprises at least partially reduced nanoparticles of A$_x$Eu$_{1-x}$VO$_4$, where A is selected from the group consisting of Y, Gd and La, and wherein $0 \leq x \leq 1$.

25. A method of detecting oxidizing species, said detecting method comprising a step of analyzing a sample of oxidizing species, said analyzing step consisting of:
  i) providing photoluminescent nanoparticles of A$_x$Eu$_{1-x}$(VO$_4$)$_y$(PO$_4$)$_{(1-y)}$, where A is one from Y, Gd and La, $0 \leq x \leq 1$ and $0 \leq y \leq 1$, said nanoparticles being chemically reduced before using a reducing agent;
  iv) thereafter introducing said nanoparticles into the assay sample,
  v) thereafter exciting said nanoparticles,
  vi) thereafter measuring the luminous intensity emitted by the sample at at least one wavelength representative of an oxidized state or of a reduced state of said nanoparticles, and
  vii) thereafter estimating the presence and/or the quantity of oxidizing species by interpreting said measurement, if applicable by reference to a standard or calibration.

26. The method as claimed in claim 25, in which said reducing agent is NaBH$_4$.

* * * * *

UNITED STATES PATENT AND TRADEMARK OFFICE
CERTIFICATE OF CORRECTION

PATENT NO. : 10,788,497 B2
APPLICATION NO. : 15/747888
DATED : September 29, 2020
INVENTOR(S) : Cédric Bouzigues et al.

Page 1 of 1

It is certified that error appears in the above-identified patent and that said Letters Patent is hereby corrected as shown below:

In the Specification

Column 9, Line 13, "$EU^{3-}$ ions is the appearance" should read -- $EU^{3+}$ ions is the appearance --

Signed and Sealed this
Eleventh Day of May, 2021

Drew Hirshfeld
*Performing the Functions and Duties of the*
*Under Secretary of Commerce for Intellectual Property and*
*Director of the United States Patent and Trademark Office*